(12) United States Patent
Bharat et al.

(10) Patent No.: US 10,279,194 B2
(45) Date of Patent: May 7, 2019

(54) HIGH-DOSE RATE BRACHYTHERAPY SYSTEM

(71) Applicant: KONINKLIJKE PHILIPS N.V., Eindhoven (NL)

(72) Inventors: Shyam Bharat, Arlington, MA (US); Ehsan Dehghan Marvast, New York, NY (US); Amir Mohammad Tahmasebi Maraghoosh, Ridgefield, CT (US); Francois Guy Gerard Marie Vignon, Croton on Hudson, NY (US); Ameet Kumar Jain, New York, NY (US); Dirk Binnekamp, Borne (NL)

(73) Assignee: Koninklijke Philips N.V., Eindhoven (NL)

( * ) Notice: Subject to any disclaimer, the term of this patent is extended or adjusted under 35 U.S.C. 154(b) by 392 days.

(21) Appl. No.: 14/914,400

(22) PCT Filed: Sep. 15, 2014

(86) PCT No.: PCT/EP2014/069627
§ 371 (c)(1),
(2) Date: Feb. 25, 2016

(87) PCT Pub. No.: WO2015/039995
PCT Pub. Date: Mar. 26, 2015

(65) Prior Publication Data
US 2016/0199668 A1    Jul. 14, 2016

Related U.S. Application Data

(60) Provisional application No. 61/879,706, filed on Sep. 19, 2013.

(30) Foreign Application Priority Data

Oct. 29, 2013    (EP) ..................... 13190590

(51) Int. Cl.
*A61N 5/10*    (2006.01)
*A61B 90/00*    (2016.01)
(Continued)

(52) U.S. Cl.
CPC ............ *A61N 5/1007* (2013.01); *A61B 8/085* (2013.01); *A61B 8/12* (2013.01); *A61B 17/3403* (2013.01);
(Continued)

(58) Field of Classification Search
CPC ...................................... A61N 5/1001–5/1029
See application file for complete search history.

(56) References Cited

U.S. PATENT DOCUMENTS 4,821,731 A    4/1989    Martinelli et al.
5,938,602 A    8/1999    Lloyd
(Continued)

FOREIGN PATENT DOCUMENTS

| CN | 1537648 A | 10/2004 |
|---|---|---|
| JP | 2007020837 A | 2/2007 |
| WO | 2013001437 A1 | 1/2013 |

OTHER PUBLICATIONS

Mung, J. et al., "A Non-disruptive technology for robust 3D tool tracking for ultrasound-guided interventions".

*Primary Examiner* — Thaddeus B Cox

(57) ABSTRACT

The invention relates to a HDR brachytherapy system comprising an ultrasound sensor for being arranged at the location of a brachytherapy catheter (12), wherein the ultrasound sensor is adapted to generate an ultrasound signal based on ultrasound radiation, which has been sent by an ultrasound imaging device preferentially comprising a TRUS probe (40) and which has been received by the ultrasound sensor. The position of the ultrasound sensor is determined based on the generated ultrasound signal, and
(Continued)

based on this position of the ultrasound sensor the pose and shape of the brachytherapy catheter and/or the position of a HDR radiation source are determined. This allows for a very accurate determination of the pose and shape of the brachytherapy catheter and/or of the position of the HDR radiation source, which in turn can lead to an improved HDR brachytherapy.

15 Claims, 10 Drawing Sheets

(51) Int. Cl.
*A61B 8/08* (2006.01)
*A61B 8/12* (2006.01)
*A61B 17/34* (2006.01)
*A61B 17/00* (2006.01)
*A61B 8/00* (2006.01)
*A61B 34/20* (2016.01)
*A61B 18/00* (2006.01)
*A61B 34/10* (2016.01)

(52) U.S. Cl.
CPC ............ *A61B 90/37* (2016.02); *A61N 5/1027* (2013.01); *A61N 5/1049* (2013.01); *A61B 8/4245* (2013.01); *A61B 8/445* (2013.01); *A61B 34/20* (2016.02); *A61B 2017/00274* (2013.01); *A61B 2017/3411* (2013.01); *A61B 2017/3413* (2013.01); *A61B 2018/00547* (2013.01); *A61B 2034/104* (2016.02); *A61B 2034/2063* (2016.02); *A61B 2090/3782* (2016.02); *A61B 2090/3929* (2016.02); *A61N 5/103* (2013.01); *A61N 5/1048* (2013.01); *A61N 5/1071* (2013.01); *A61N 2005/1024* (2013.01); *A61N 2005/1058* (2013.01); *A61N 2005/1061* (2013.01)

(56) References Cited

U.S. PATENT DOCUMENTS

| | | |
|---|---|---|
| 6,587,709 B2 | 7/2003 | Solf et al. |
| 7,267,650 B2 | 9/2007 | Chow et al. |
| 9,101,395 B2 | 8/2015 | Gutierrez et al. |
| 2003/0060700 A1* | 3/2003 | Solf ................ A61B 8/0833 600/411 |
| 2003/0135102 A1 | 7/2003 | Burdette et al. |
| 2006/0258895 A1 | 11/2006 | Maschke |
| 2008/0275341 A1 | 11/2008 | Fehre et al. |
| 2009/0156893 A1 | 6/2009 | Bourne et al. |
| 2010/0312141 A1* | 12/2010 | Keast ............... A61B 10/0266 600/567 |
| 2011/0166410 A1 | 7/2011 | Gutierrez et al. |
| 2013/0102891 A1 | 4/2013 | Binnekamp et al. |
| 2013/0131503 A1 | 5/2013 | Schneider et al. |
| 2013/0204072 A1 | 8/2013 | Verard et al. |
| 2013/0218024 A1 | 8/2013 | Boctor et al. |
| 2014/0005465 A1 | 1/2014 | Ribbing |
| 2014/0121502 A1 | 5/2014 | Vignon et al. |
| 2015/0150459 A1* | 6/2015 | Werahera ............ A61B 5/0075 600/411 |

* cited by examiner

HIGH-DOSE RATE BRACHYTHERAPY SYSTEM

CROSS-REFERENCE TO PRIOR APPLICATIONS

This application is the U.S. National Phase application under 35 U.S.C. § 371 of International Application Serial No. PCT/EP2014/069627, filed on Sep. 15, 2014, which claims the benefit of U.S. Application Ser. No. 61/879,706, filed on Sep. 19, 2013 and European Patent Application 13190590.3 filed on Oct. 29, 2013. These applications are hereby incorporated by reference herein.

FIELD OF THE INVENTION

The invention relates to a high-dose rate (HDR) brachytherapy system for performing a HDR brachytherapy. The invention further relates to a HDR brachytherapy method and a computer program for performing the HDR brachytherapy by using the HDR brachytherapy system.

BACKGROUND OF THE INVENTION

HDR brachytherapy is a form of cancer therapy that utilizes high doses of ionizing radiation delivered over a short period of time, i.e., for instance, in some minutes, directly at or near the target. Since the delivered doses are relatively high, only a very small margin of error regarding dwell positions, where the doses are applied, and dwell times defining the time periods of applying the doses at the dwell positions is acceptable. It is therefore essential to be able to develop an accurate treatment plan, which defines the dwell positions and the dwell times, and to accurately deliver radiation according to this treatment plan. The treatment plan is generally developed based on a segmented ultrasound image in which the target and the brachytherapy catheters used for delivering the doses are segmented. For developing a very accurate treatment plan it is therefore required to very accurately segment the target and the brachytherapy catheters in the ultrasound image. However, the inherent ultrasonic contrast between a) the target and the brachytherapy catheters and b) their surrounding is often relatively low, which may lead to a not very accurate segmentation of the target and the brachytherapy catheters in the ultrasound image and, thus, to a not very accurate HDR brachytherapy.

SUMMARY OF THE INVENTION

It is an object of the present invention to provide a HDR brachytherapy system for performing a HDR brachytherapy, which allows for an improved accuracy of performing the HDR brachytherapy. It is a further object of the present invention to provide a HDR brachytherapy method and computer program for performing the HDR brachytherapy by using the HDR system.

In a first aspect of the present invention a HDR brachytherapy system for performing a HDR brachytherapy is presented, wherein the HDR brachytherapy system comprises:

a brachytherapy catheter to be inserted into or close to a target region inside a living being, an elongated introduction element with a radiation source for applying radiation emitted by the radiation source to the target region, wherein the brachytherapy catheter and the introduction element are adapted to allow the introduction element to be introduced into the brachytherapy catheter, an ultrasound imaging device for generating an ultrasound image of the inside of the living being by sending ultrasound radiation into the inside of the living being and by measuring ultrasound radiation reflected by the inside of the living being, an ultrasound sensor for being arranged at the location of the brachytherapy catheter within the living being, wherein the ultrasound sensor is adapted to generate an ultrasound signal based on ultrasound radiation sent by the ultrasound imaging device and received by the ultrasound sensor, a position determining unit for determining the position of the ultrasound sensor based on the generated ultrasound signal and for determining the pose and shape of the brachytherapy catheter within the living being and/or the position of the radiation source, when the introduction element has been introduced into the brachytherapy catheter, based on the determined position of the ultrasound sensor.

Since the ultrasound sensor is arranged at the location of the brachytherapy catheter within the living being, when the ultrasound signal is generated, wherein the position of the ultrasound sensor can accurately be determined based on the generated ultrasound signal, and since the pose and shape of the brachytherapy catheter within the living being and/or the position of the radiation source, when the introduction element with the radiation source has been introduced into the brachytherapy catheter, is determined based on the accurately determined position of the ultrasound sensor, the pose and shape of the brachytherapy catheter and/or the position of the radiation source can be accurately determined, without necessarily requiring a segmentation of the ultrasound image. This allows for an accurate determination of a treatment plan and an accurate delivery of the radiation according to the treatment plan based on the accurately determined pose and shape of the brachytherapy catheter and/or the accurately determined position of the radiation source.

The elongated introduction element is preferentially a source cable being adapted to move the radiation source within the brachytherapy catheter. The ultrasound imaging device is preferentially a two-dimensional or a three-dimensional ultrasound imaging device. It may comprise a transrectal ultrasound (TRUS) probe. The ultrasound sensor is, for instance, a lead zirconate titanate (PZT) ultrasound sensor.

The HDR brachytherapy system can comprise one or several brachytherapy catheters. Moreover, one or several ultrasound sensors can be arranged at the location of the respective brachytherapy catheter within the living being. In particular, the HDR brachytherapy system can comprise several ultrasound sensors for being arranged at the location of the brachytherapy catheter within the living being, wherein the ultrasound sensors are adapted to generate ultrasound signals based on the ultrasound radiation sent by the ultrasound imaging device and received by the ultrasound sensor, wherein the position determining unit can be adapted to determine the position of the brachytherapy catheter within the living being based on the generated ultrasound signals. The living being is preferentially a person, but can also be an animal.

The HDR brachytherapy system may comprise a guidewire equipped with the ultrasound sensor, wherein the guidewire may be adapted to be inserted into the brachytherapy catheter for arranging the ultrasound sensor at the location of the brachytherapy catheter within the living being. Preferentially, the guidewire is equipped with an ultrasound sensor arranged at the tip of the guidewire. In particular, the guidewire may be equipped with a single ultrasound sensor only, which is arranged at the tip of the guidewire. However, in an embodiment the guidewire may be equipped with at least one further ultrasound sensor not arranged at the tip of the guidewire. Alternatively or in addition, the brachytherapy catheter may be equipped with the ultrasound sensor for arranging the ultrasound sensor at the location of the brachytherapy catheter and/or the introduction element may be equipped with the ultrasound sensor such that the ultrasound sensor is arranged at the location of the brachytherapy catheter, when the introduction element has been introduced into the brachytherapy catheter.

In an embodiment a guidewire is equipped with the ultrasound sensor, wherein the guidewire is adapted to be inserted into the brachytherapy catheter for arranging the ultrasound sensor at the location of the brachytherapy catheter within the living being, wherein the guidewire is adapted to be inserted into and retracted from the brachytherapy catheter, wherein the ultrasound sensor is adapted to generate ultrasound signals, while the guidewire is inserted into and/or retracted from the brachytherapy catheter, and wherein the position determining unit is adapted to determine different positions of the ultrasound sensor based on the ultrasound signals generated while the guidewire is inserted into and/or refracted from the brachytherapy catheter and to determine the pose and shape of the brachytherapy catheter based on the determined positions of the ultrasound sensor. This allows determining the pose and shape of the brachytherapy catheter by using only a single ultrasound sensor, which is preferentially arranged at the tip of the guidewire.

The ultrasound imaging device is preferentially adapted such that during the movement of the guidewire the ultrasound sensor is in the field of view of the ultrasound imaging device, in order to allow the ultrasound sensor to generate the ultrasound signal at each position, which should be used for determining the pose and shape of the brachytherapy catheter. The ultrasound imaging device is therefore preferentially a three-dimensional ultrasound imaging device. However, the ultrasound imaging device can also be a two-dimensional ultrasound imaging device, if an ultrasound sensor attached to a guidewire is used for determining the position and shape of the brachytherapy catheter. In particular, the ultrasound imaging device can be a two-dimensional ultrasound imaging device for generating a two-dimensional image of an imaging plane within the living being, wherein the position of the imaging plane is modifiable, in order to send ultrasound radiation into different regions within the living being for allowing the ultrasound sensor to generate the ultrasound signals, while the ultrasound sensor is at the different positions during the insertion and/or retraction of the guidewire, wherein the system can further comprise an imaging plane position providing unit for providing the respective position of the imaging plane and a guidewire control unit for controlling the insertion and/or retraction of the guidewire based on the determined position of the imaging plane such that the ultrasound sensor is within the imaging plane, when the position of the imaging plane is modified, wherein the position determining unit is adapted to determine the positions of the ultrasound sensor based on the generated ultrasound signals and the provided respective positions of the imaging plane. This allows determining the position and shape of the brachytherapy catheter by using a guidewire equipped with a single ultrasound sensor only, even if the ultrasound imaging device is a two-dimensional ultrasound imaging device.

In a further embodiment the guidewire is equipped with several ultrasound sensors, wherein each ultrasound sensor is adapted to generate an ultrasound signal based on ultrasound radiation sent by the ultrasound imaging device and received by the respective ultrasound sensor, wherein the position determining unit is adapted to a) determine for each ultrasound sensor a set of different positions of the respective ultrasound sensor based on the respective ultrasound signals generated during the insertion and/or retraction of the guidewire, b) determine for each set of different positions of the respective ultrasound sensor a pose and shape of the brachytherapy catheter, thereby determining a set of poses and shapes of the brachytherapy catheter, and c) average the poses and shapes of the determined set of poses and shapes of the brachytherapy catheter for determining an average pose and shape of the brachytherapy catheter. This can further improve the accuracy of determining the pose and shape of the brachytherapy catheter.

The position determination unit can be adapted to determine the pose and shape of the brachytherapy catheter based on the determined positions of the ultrasound sensor by fitting a curve, which models the brachytherapy catheter, to the determined positions of the ultrasound sensor. The fitting procedure can consider constraints imposed by known mechanical characteristics of the brachytherapy catheter like a maximally possible bending of the brachytherapy catheter. Also this can lead to a further improved accuracy of the determined pose and shape of the brachytherapy catheter.

In an embodiment the system comprises several ultrasound sensors for being arranged along the length of the brachytherapy catheter, wherein each ultrasound sensor is adapted to generate an ultrasound signal based on ultrasound radiation sent by the ultrasound imaging device and received by the respective ultrasound sensor, wherein the position determining unit is adapted to determine the positions of the ultrasound sensors based on the ultrasound signals generated by the ultrasound sensors and to determine the pose and shape of the brachytherapy catheter based on the determined positions. For instance, the guidewire may be equipped with several ultrasound sensors, wherein each ultrasound sensor may be adapted to generate an ultrasound signal based on ultrasound radiation sent by the ultrasound imaging device and received by the respective ultrasound sensor, wherein the position determining unit can be adapted to determine the positions of the ultrasound sensors based on the ultrasound signals generated by the ultrasound sensors, when the guidewire has been inserted into the brachytherapy catheter, and to determine the pose and shape of the brachytherapy catheter based on the determined positions. Alternatively or in addition, the brachytherapy catheter may be equipped with several ultrasound sensors, wherein each ultrasound sensor may be adapted to generate an ultrasound signal based on ultrasound radiation sent by the ultrasound imaging device and received by the respective ultrasound sensor, wherein the position determining unit may be adapted to determine the positions of the ultrasound sensors based on the ultrasound signals generated by the ultrasound sensors and to determine the pose and shape of the brachytherapy catheter based on the determined positions. This allows determining the pose and shape of the brachytherapy catheter very accurately, without requiring to move the guidewire or the brachytherapy catheter during the determination of the pose and shape of the brachytherapy catheter. In particular, if the brachytherapy catheter is equipped with several ultrasound sensors arranged along the length of the brachytherapy catheter, the pose and shape of the brachytherapy catheter can be determined during the brachytherapy, i.e. while the radiation source is moved within the brachytherapy catheter, very accurately.

For this determination a three-dimensional ultrasound imaging device can be used, wherein all ultrasound sensors, which should be used for determining the pose and shape of the brachytherapy catheter, are arranged within the field of view of the ultrasound imaging device. However, instead of using the three-dimensional ultrasound imaging device also for determining the pose and shape of the brachytherapy catheter based on several ultrasound sensors a two-dimensional ultrasound imaging device may be used. In particular, the ultrasound imaging device can be a two-dimensional ultrasound imaging device for generating a two-dimensional image of an imaging plane within the living being, wherein the position of the imaging plane is modifiable, in order to send ultrasound radiation into different regions within the living being for allowing the several ultrasound sensors to generate ultrasound signals based on the ultrasound radiation sent by the ultrasound imaging device and received by the respective ultrasound sensor, wherein the system may further comprise an imaging plane position providing unit for providing the respective position of the imaging plane, wherein the position determining unit may be adapted to determine the positions of the ultrasound sensors based on the respective ultrasound signals generated by the ultrasound sensors and the determined respective positions of the imaging plane. Thus, the positions of the ultrasound sensors can be determined by moving the imaging plane defined by the two-dimensional ultrasound imaging device such that each ultrasound sensor, which should be used for determining the pose and shape of the brachytherapy catheter, is at least one time within the imaging plane, wherein the position of the imaging plane may be modified by moving, in particular, translating and/or rotating, the two-dimensional ultrasound imaging device. This allows determining the pose and shape of the brachytherapy catheter based on a determination of the positions of ultrasound sensors arranged along the length of the brachytherapy catheter, without necessarily requiring a three-dimensional ultrasound imaging device having a field of view covering the positions of the different ultrasound sensors.

Also in this embodiment the position determining unit may be adapted to determine the pose and shape of the brachytherapy catheter by fitting a curve modeling the pose and shape of the brachytherapy catheter to the determined positions of the ultrasound sensors. Moreover, also this fitting procedure can consider constraints imposed by known mechanical characteristics of the brachytherapy catheter like a maximally possible bending of the brachytherapy catheter. This can further improve the accuracy of determining the pose and shape of the brachytherapy catheter.

In an embodiment the introduction element is equipped with the ultrasound sensor such that the ultrasound sensor is arranged within the brachytherapy catheter, when the introduction element has been introduced into the brachytherapy catheter, wherein the system further comprises a spatial relation providing unit for providing a spatial relation between the ultrasound sensor and the radiation source, wherein the position determining unit is adapted to determine the position of the radiation source, when the introduction element has been introduced into the brachytherapy catheter, based on the generated ultrasound signal and the provided spatial relation. The spatial relation providing unit may be a storing unit, in which the spatial relation between the ultrasound sensor and the radiation source, which has been predetermined, is stored already. The introduction element may be equipped with one or several ultrasound sensors.

The system preferentially comprises a display for displaying a determined position of the radiation source on the generated ultrasound image. It is further preferred that the system comprises a treatment plan providing unit for providing a treatment plan defining planned dwell positions within the living being, at which the radiation source should be arranged, wherein the system is adapted to also show the planned dwell positions on the generated image. This allows a user to observe deviations between planned dwell positions and real actual dwell positions, wherein the user may correct the actual position of the radiation source and/or stop the actual HDR brachytherapy, if the observed deviations are not acceptable for the user.

The system preferentially further comprises a treatment plan providing unit for providing a treatment plan defining planned dwell positions within the living being, at which the radiation source should be arranged, wherein the position determining unit is adapted to determine the positions of the radiation source, when the radiation source is supposed to be placed at the planned dwell positions during the HDR brachytherapy, as real dwell positions, wherein the treatment plan providing unit is adapted to modify the treatment plan based on the determined real dwell positions. In particular, the treatment plan providing unit can be adapted to provide an original treatment plan defining dwell positions and dwell times and to compute a dose distribution based on the real dwell positions and the real dwell times, i.e. based on the dwell positions and the dwell times which have really been achieved, and the future dwell positions and future dwell times defined by the original treatment plan. The treatment plan providing unit can be further adapted to determine whether this computed dose distribution meets predefined dose requirements. For instance, it can be checked whether the computed dose distribution leads to a radiation dose applied to the target region being larger than a predefined threshold and to a radiation dose applied to surrounding elements, in particular, to surrounding organs at risk, being smaller than a predefined threshold. If this is not the case, the future dwell positions and the future dwell times and a corresponding dose distribution can be recalculated such that the predefined dose requirements are fulfilled. Thus, the treatment plan can be adapted to the actual real positions of the radiation source, which can allow for a further improved HDR brachytherapy.

The system may comprise an introduction element controller for controlling the introduction and/or retraction of the introduction element into and/or from, respectively, the brachytherapy catheter based on the determined position of the radiation source. In particular, if the system further comprises a treatment plan providing unit for providing a treatment plan defining planned dwell positions within the living being, at which the radiation source should be arranged, and dwell times indicating the respective time period the radiation source should be arranged at the respective planned dwell position, the position determining unit can be adapted to determine the positions of the radiation source, when the radiation source is supposed to be placed at the planned dwell positions during the HDR brachytherapy, as real dwell positions, wherein the introduction element controller can be adapted to control the introduction and/or refraction of the introduction element based on the real dwell positions and the planned dwell positions such that the planned dwell positions are reached as accurately as possible. Also this can further improve the accuracy of the HDR brachytherapy procedure.

In an embodiment the brachytherapy catheter is equipped with the ultrasound sensor, wherein the system further comprises a spatial relation providing unit for providing a spatial relation between the ultrasound sensor and the radiation source, when the introduction element has been introduced into the brachytherapy catheter, wherein the position determining unit is adapted to determine the position of the radiation source, when the introduction element has been introduced into the brachytherapy catheter, based on the generated ultrasound signal and the provided spatial relation. In particular, the spatial relation providing unit can be adapted to provide the spatial relation between the ultrasound sensor and the radiation source, when the introduction element has been introduced into the brachytherapy catheter as far as possible, i.e. the spatial relation providing unit can provide the spatial relation between the ultrasound sensor and the first dwell position. Correspondingly, the position determining unit can be adapted to determine the position of the radiation source, when the introduction element has been introduced into the brachytherapy catheter as far as possible, i.e. to determine the first dwell position of the radiation source. The spatial relation providing unit can also be adapted to determine the spatial relation between the ultrasound sensor and the radiation source based on the actual position of the introduction element relative to the brachytherapy catheter and based on a known spatial relation between the ultrasound sensor and the brachytherapy catheter. The actual location of the introduction element relative to the brachytherpay catheter can be provided by an afterloader comprising a motor for moving the introduction element within the brachytherapy catheter. Thus, also if the ultrasound sensor is a part of the brachytherapy catheter, the position of the radiation source can reliably be determined based on the ultrasound signal generated by the ultrasound sensor.

In an embodiment the brachytherapy catheter is equipped with the ultrasound sensor at a longitudinal position of the brachytherapy catheter such that the radiation source is arrangeable at the longitudinal position, at which the ultrasound sensor is located, when the introduction element is introduced into the brachytherapy catheter, wherein the position determining unit is adapted to detect a change of the generated ultrasound signal, when the radiation source is arranged at the longitudinal position, at which the ultrasound sensor is located, and to determine the position of the radiation source based on the determined position of the ultrasound sensor and the detected change of the ultrasound signal. Since the ultrasound signal changes, when the radiation source has reached the longitudinal position at which the ultrasound sensor is located, the position of the ultrasound sensor, which is determined while the change of the ultrasound signal is detected, is the actual position of the radiation source. This allows determining the actual position of the radiation source, without necessarily requiring a predetermined spatial relation between the ultrasound sensor and the radiation source.

In a further aspect of the present invention a HDR brachytherapy method for performing a HDR brachytherapy by using the HDR brachytherapy system as defined in claim 1 is presented, wherein the HDR brachytherapy method comprises:

generating an ultrasound image of the inside of a living being by sending ultrasound radiation into the inside of the living being and by measuring ultrasound radiation reflected by the inside of the living being by an ultrasound imaging device, generating an ultrasound signal by an ultrasound sensor, which is arranged at the location of the brachytherapy catheter within the living being, wherein the ultrasound sensor generates the ultrasound signal based on ultrasound radiation sent by the ultrasound imaging device and received by the ultrasound sensor, determining the position of the ultrasound sensor based on the generated ultrasound signal by the position determining unit, and determining the pose and shape of the brachytherapy catheter within the living being and/or the position of the radiation source, when the introduction element has been introduced into the brachytherapy catheter, based on the determined position of the ultrasound sensor by the position determining unit.

In a further aspect of the present invention a computer program for performing a HDR brachytherapy by using the HDR brachytherapy system as defined in claim 1 is presented, wherein the computer program comprises program code means for causing the HDR brachytherapy system to carry out the steps of the HDR brachytherapy method as defined in claim 14, when the computer program is run on a computer controlling the HDR brachytherapy system.

It shall be understood that the brachytherapy system of claim 1, the brachytherapy method of claim 14, and the computer program of claim 15 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
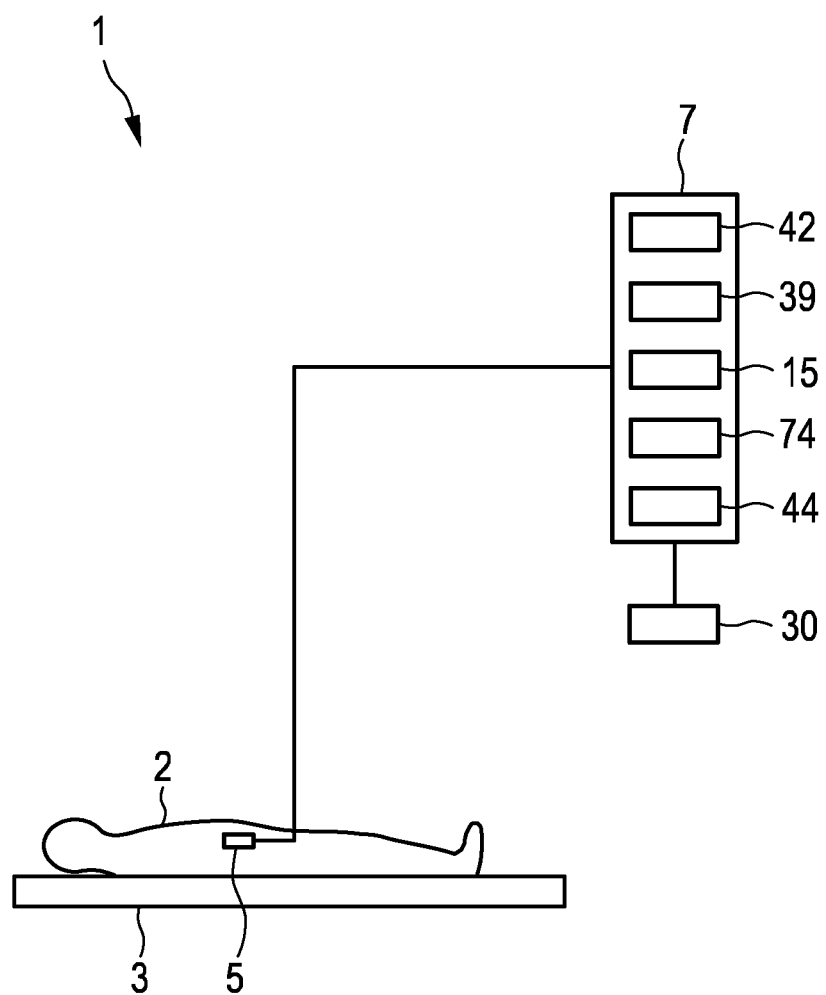
FIG. 1 shows schematically and exemplarily an embodiment of a HDR brachytherapy system for performing a HDR brachytherapy.
Figure 2:
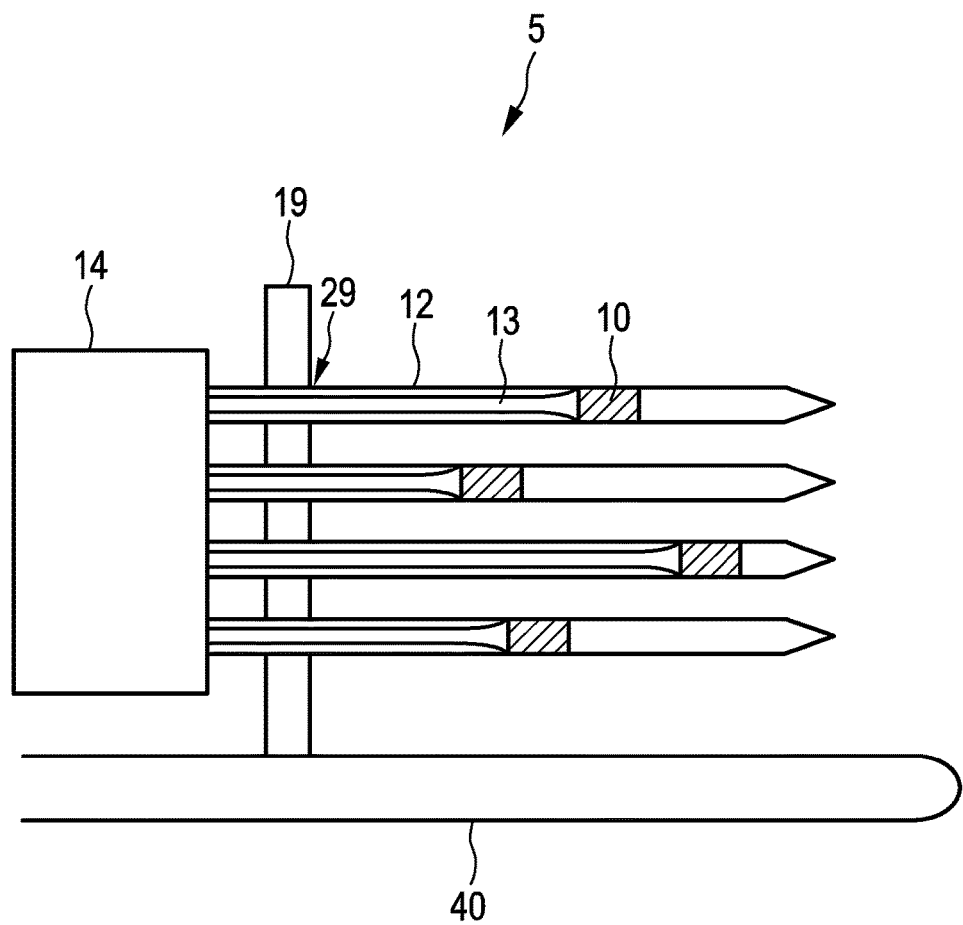
FIG. 2 shows schematically and exemplarily a placing unit of the HDR brachytherapy system.

FIG. 1 schematically and exemplarily shows an embodiment of a HDR brachytherapy system for applying a HDR brachytherapy to a living object. In this embodiment the HDR brachytherapy system 1 is adapted to apply a brachytherapy to a prostate of a person 2 lying on a table 3. The brachytherapy system 1 comprises a placing unit 5 for being partly inserted into the person 2 and for placing radiation sources close to or within the prostate for directing radiation emitted by the radiation sources to the prostate. The placing unit 5 is exemplarily and schematically shown in more detail in FIG. 2.

The placing unit 5 comprises several brachytherapy catheters 12 for being inserted into the person 2. The placing unit 5 further comprises several introduction elements 13 being wires to which the radiation sources 10 are attached, wherein a respective wire 13 can be moved within a respective brachytherapy catheter 12 for placing a respective radiation source 10 at a desired dwell position. The brachytherapy catheters 12 with the wires 13 are attached to a motor unit 14 comprising several motors for moving the wires 13 in a forward direction and in a backward direction for placing the radiation sources 10 at desired dwell positions. The radiation sources 10 preferentially comprise radioactive material emitting radioactive radiation like Ir-192. However, other radiation sources can also be used for performing the HDR brachytherapy.

The brachytherapy catheters 12 may be flexible or rigid. They have a central hollow channel through which the radiation sources 10 can be moved. In particular, a brachytherapy catheter may be a plastic flexible hollow device having, for instance, an outer diameter of about 2 mm, an inner diameter of about 1.5 mm and a length of approximately 25 cm. The brachytherapy catheters 12 preferentially have a flat opening at one end through which the radiation sources 10 can be introduced. The other end of the brachytherapy catheters 12 is preferentially closed in the form of a beveled tip. This is to ensure that the radiation sources 10 do not come in direct contact with the tissue.

Figure 3:
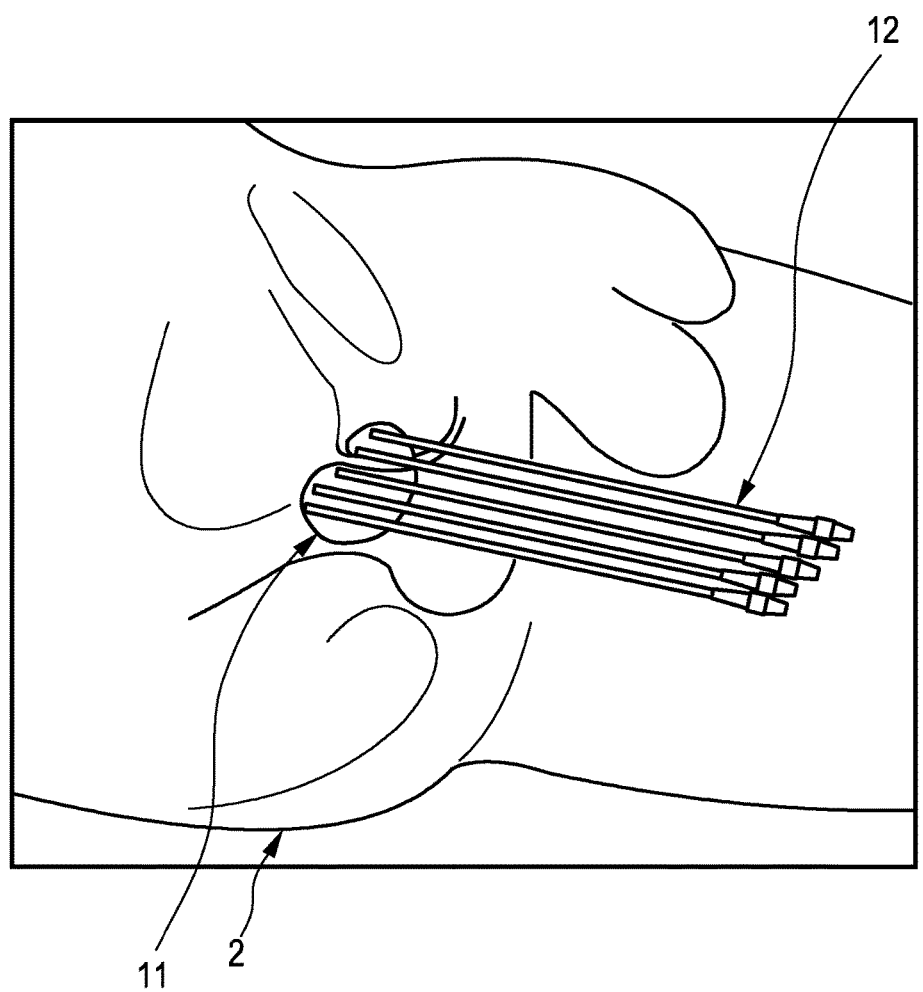
FIG. 3 shows schematically and exemplarily several brachytherapy catheters of the brachytherapy system inserted into the prostate of a person, FIG. 4 schematically and exemplarily illustrates an arrangement of the placing unit equipped with a TRUS probe with respect to the person.

The placing unit 5 further comprises a template 19, which can be used for inserting the brachytherapy catheters 12 in a more uniform configuration into the person 2. The brachytherapy catheters 12 are held in openings 29 in the template 19, which are arranged in a rectangular grid. FIG. 3 shows schematically and exemplarily a possible arrangement of the brachytherapy catheters 12 of the placing unit 5 within the prostate 11.

Figure 4:
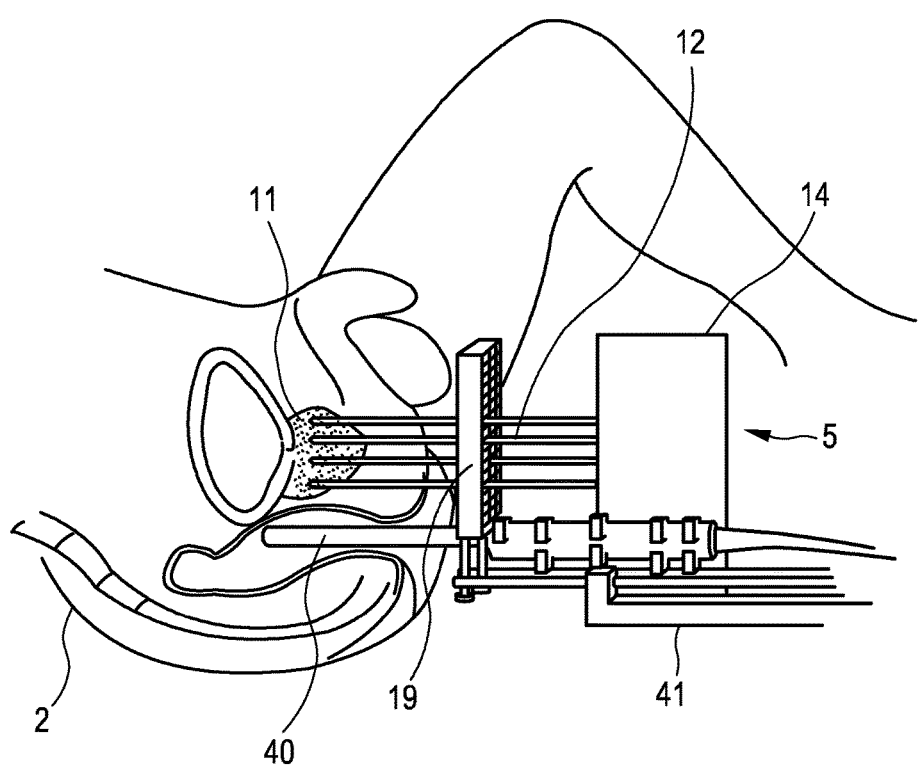

An ultrasound data generating unit 40 for generating ultrasound data of the prostate 11 is attached to the placing unit 5. In this embodiment the ultrasound data generating unit 40 is a three-dimensional TRUS probe 40 sending ultrasound radiation into a three-dimensional region to be imaged. The arrangement of the placing unit 5 with the TRUS probe 40 during the HDR brachytherapy is schematically and exemplarily illustrated in FIG. 4. The TRUS probe 40 and the placing unit 5 are held by a holding element 41. The TRUS probe 40 is connected to an ultrasound image generating unit 42, which is located in a processing and control device 7, for generating an ultrasound image based on the ultrasound data generated by the TRUS probe 40.

The HDR brachytherapy system 1 further comprises an ultrasound sensor for being arranged at the location of the brachytherapy catheter 12 within the person 2, wherein the ultrasound sensor is adapted to generate an ultrasound signal based on ultrasound radiation sent by the TRUS probe 40 and received by the ultrasound sensor, and a position determining unit 44 for determining the position of the ultrasound sensor based on the generated ultrasound signal and for determining the pose and shape of the brachytherapy catheter 12 within the living being 2 based on the determined position of the ultrasound sensor.

Figure 5:
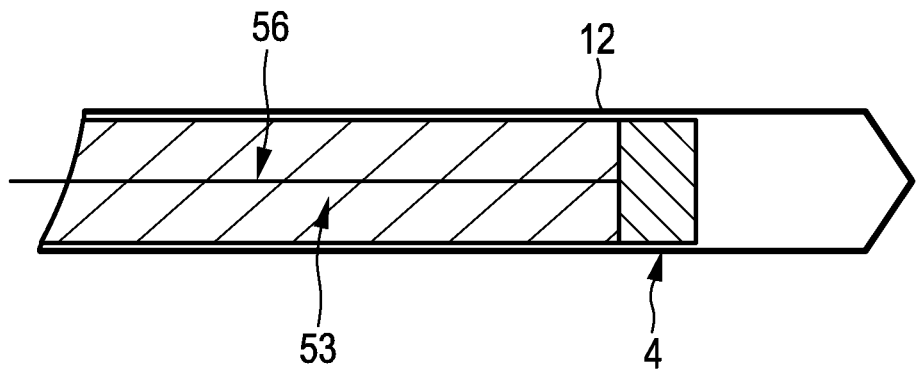
FIG. 5 shows schematically and exemplarily an embodiment of a guidewire inserted into a brachytherapy catheter.

In this embodiment the HDR brachytherapy system 1 comprises a guidewire 53 equipped with the ultrasound sensor 4 as schematically and exemplarily illustrated in FIG. 5, wherein the guidewire 53 is adapted to be inserted into a respective brachytherapy catheter 12 for arranging the ultrasound sensor 4 at the location of the respective brachytherapy catheter 12 within the person 2. The guidewire 53 is equipped with a single ultrasound sensor 4 arranged at the tip of the guidewire 53 and electrically connected to the position determining unit 44 via an electrical connection 56, wherein the guidewire 53 is inserted into and retracted from the respective brachytherapy catheter 12 and wherein the ultrasound sensor 4 is adapted to generate the ultrasound signals, while the guidewire 53 is inserted into and/or retracted from the brachytherapy catheter 12. The position determining unit 44 is adapted to determine different positions of the ultrasound sensor 4 based on the ultrasound signals generated while the guidewire 53 is inserted into and/or retracted from the respective brachytherapy catheter 12 and to determine the pose and shape of the brachytherapy catheter 12 based on the determined positions of the ultrasound sensor 4. This can be performed for each brachytherapy catheter 12, in order to determine for each brachytherapy catheter 12 the respective pose and shape. For determining the respective pose and shape of the respective brachytherapy catheter 12 based on the positions of the ultrasound sensor determined while the guidewire 53 is inserted into and/or retracted from the respective brachytherapy catheter 12, a curve modeling the respective brachytherapy catheter 12 can be fitted to the determined positions of the ultrasound sensor 4. During the fitting procedure constraints imposed by mechanical characteristics of the respective brachytherapy catheter 12 like a maximally possible bending of the respective brachytherapy catheter 12 may be used.

Thus, an ultrasound sensor 4 arranged at the tip of a guidewire 53 may be used for performing a pre-procedural brachytherapy catheter mapping, wherein the guidewire 53 is sequentially inserted into each brachytherapy catheter 12. The guidewire 53 with the ultrasound sensor 4 and the brachytherapy catheters 12 are preferentially adapted such that the guidewire 53 with the ultrasound sensor 4 can access the tip of the respective brachytherapy catheter 12, wherein the diameter of the guidewire 53 with the ultrasound sensor 4 preferentially matches the inner diameter of the respective brachytherapy catheter 12, in order to ensure a snug fit.

As the guidewire 53 is inserted into and/or retracted from the brachytherapy catheter, the determined positions of the ultrasound sensor 4 are stored and can already be regarded as representing the three-dimensional pose and shape of the respective brachytherapy catheter. Thus, the position determining unit 44 can be adapted to determine the three-dimensional pose and shape of the brachytherapy catheter as already being the determined sequence of positions of the ultrasound sensor 4. However, the position determining unit 44 can also be adapted to apply a more sophisticated algorithm to the determined positions of the ultrasound sensor 4 for determining the three-dimensional pose and shape of the respective brachytherapy catheter. For instance, as already mentioned above, the determined positions of the ultrasound sensor can be fitted under constraints imposed by known mechanical characteristics of the brachytherapy catheters 12.

In a further embodiment, a guidewire 153 equipped with several ultrasound sensors 4 may be used for the pre-procedural brachytherapy catheter mapping. Such a guidewire 153 with several ultrasound sensors 4 electrically connected with the position determining unit 44 via electrical connections 56 and introduced into a brachytherapy catheter 12 is exemplarily and schematically illustrated in FIG. 6. In this embodiment one ultrasound sensor 4 is arranged at the tip of the guidewire 153 and other ultrasound sensors 4 are distributed along the length of the guidewire 153. Each ultrasound sensor 4 is adapted to generate an ultrasound signal based on ultrasound radiation sent by the TRUS probe 40 and received by the respective ultrasound sensor 4, wherein the position determining unit 44 is adapted to determine for each ultrasound sensor 4 a set of different positions of the respective ultrasound sensor 4 based on the respective ultrasound signals generated during the insertion and/or retraction of the guidewire 153 in the respective brachytherapy catheter 12. The position determining unit 44 is further adapted to determine for each set of different positions of the respective ultrasound sensor 4 a respective pose and shape of the respective brachytherapy catheter 12, in order to determine a set of poses and shapes of the respective brachytherapy catheter 12, and to average the poses and shapes of the determined set of poses and shapes of the respective brachytherapy catheter 12 for determining an average pose and shape of the respective brachytherapy catheter 12. In particular, each set of different positions of the respective ultrasound sensor can already be regarded as representing a pose and shape of the respective brachytherapy catheter such that averaging the poses and shapes of the respective brachytherapy catheter can be performed by averaging the positions determined for different ultrasound sensors, in order to determine the average pose and shape. This averaging procedure may be performed, if the guidewire of 153 is equipped with two or three ultrasound sensors, wherein one ultrasound sensor 4 is located at the tip of the guidewire 153.

If in an embodiment the guidewire is equipped with several ultrasound sensors 4, in particular, with four or more ultrasound sensors 4, wherein preferentially one ultrasound sensor 4 is located at the tip of the guidewire 153 and the other ultrasound sensors 4 are distributed along the length of the guidewire 153, the positions of the ultrasound sensors 4 may be determined in a stationary situation, i.e. when the guidewire 153 has been inserted into the respective brachytherapy catheter 12, wherein a polynomial fit can be performed based on the determined positions of the ultrasound sensors 4, in order to determine the three-dimensional pose and shape of the respective brachytherapy catheter. Thus, in this example the three-dimensional pose and shape of the respective brachytherapy catheter 12 may be determined, without determining the positions of the ultrasound sensors 4 of the guidewire 153 during the insertion and/or the retraction of the guidewire 153.

Figure 7:
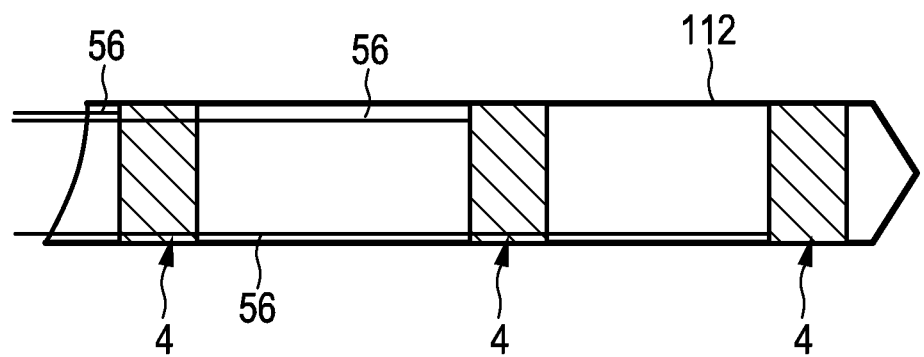
FIG. 7 shows schematically and exemplarily an embodiment of a brachytherapy catheter with several ultrasound sensors.

In a further embodiment each brachytherapy catheter 112 may be equipped with several ultrasound sensors 4 arranged along the length of the respective brachytherapy catheter 112 as schematically and exemplarily illustrated in FIG. 7. Each ultrasound sensor 4 of the respective brachytherapy catheter 112 is adapted to generate an ultrasound signal based on the ultrasound radiation sent by the TRUS probe 40 and received by the respective ultrasound sensor 4, wherein the position determining unit 44 can be adapted to determine the positions of the ultrasound sensors 4 based on the ultrasound signals generated by the ultrasound sensors 4 and to determine the pose and shape of the respective brachytherapy catheter 112 based on the determined positions. In order to provide the generated ultrasound signals to the position determining unit 44 the ultrasound sensors 4 are connected with the position determining unit 44 via electrical connections 56, which may be embedded in the wall of the brachytherapy catheter.

If the respective brachytherapy catheter 112 is equipped with multiple ultrasound sensors 4, the pose and shape of the respective brachytherapy catheter 112 can be determined during the interventional procedure, i.e. this embodiment is suited for intra-procedural brachytherapy catheter mapping. Moreover, it allows for a realtime three-dimensional brachytherapy catheter pose and shape determination, without the need for a user to insert and/or retract a tracked guidewire. At any point in time the individual ultrasound sensor positions can be determined and a polynomial function or another curve can be fitted to these determined positions, in order to determine the three-dimensional pose and shape of the respective brachytherapy catheter 112. For instance, the three-dimensional poses and shapes of the brachytherapy catheters 112 can be monitored during the delivery of the treatment, particularly to check for deviations from a pre-delivery configuration. The fitting procedure can use a constrained optimization algorithm to reconstruct the respective brachytherapy catheter pose and shape from the individual ultrasound sensor positions, wherein constraints can be used like a maximally allowed bend of the respective brachytherapy catheter 112 and/or restrictions on crossovers between multiple brachytherapy catheters 112.

Figure 6:
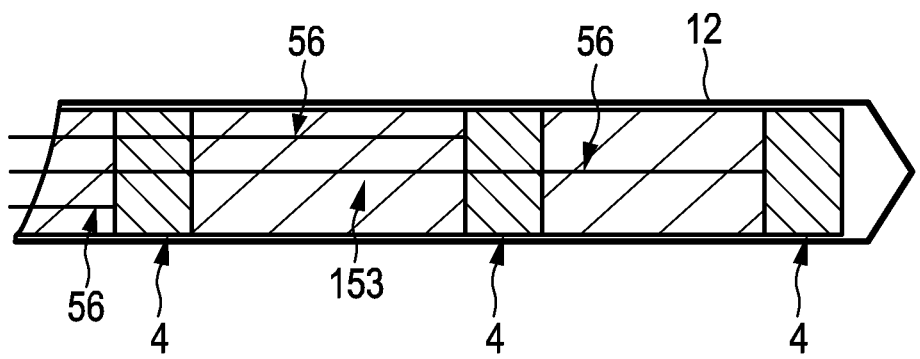
FIG. 6 shows schematically and exemplarily a further embodiment of a guidewire inserted into a brachytherapy catheter.

Although in the embodiments described with reference to FIGS. 5 to 7 the guidewires 53, 153 equipped with the ultrasound sensors 4 or the brachytherapy catheter 112 equipped with the ultrasound sensors 4 are used together with a three-dimensional TRUS probe 40, in other embodiments also a two-dimensional TRUS probe may be used for determining the three-dimensional pose and shape of the respective brachytherapy catheter. For instance, in an embodiment the guidewire 153 comprising several ultrasound sensors 4 as schematically and exemplarily illustrated in FIG. 6 is used and the TRUS probe 40 together with the ultrasound image generating unit 42 is adapted to generate a two-dimensional image of an imaging plane 6 within the person 2, wherein the position of the imaging plane 6 is modifiable, in order to send ultrasound radiation into different regions within the person 2 for allowing the several ultrasound sensors 4 to generate ultrasound signals based on the ultrasound radiation sent by the TRUS probe 40 and received by the respective ultrasound sensor 4. An imaging plane position providing unit 75 may determine the respective position of the imaging plane 6 and the position determining unit 44 may be adapted to determine the positions of the ultrasound sensors 4 based on the respective ultrasound signals generated by the ultrasound sensors 4 and the determined respective positions of the imaging plane 6, wherein these determined positions of the ultrasound sensors 4 can in turn be used for determining the three-dimensional pose and shape of the respective brachytherapy catheter 12.

Figure 8:
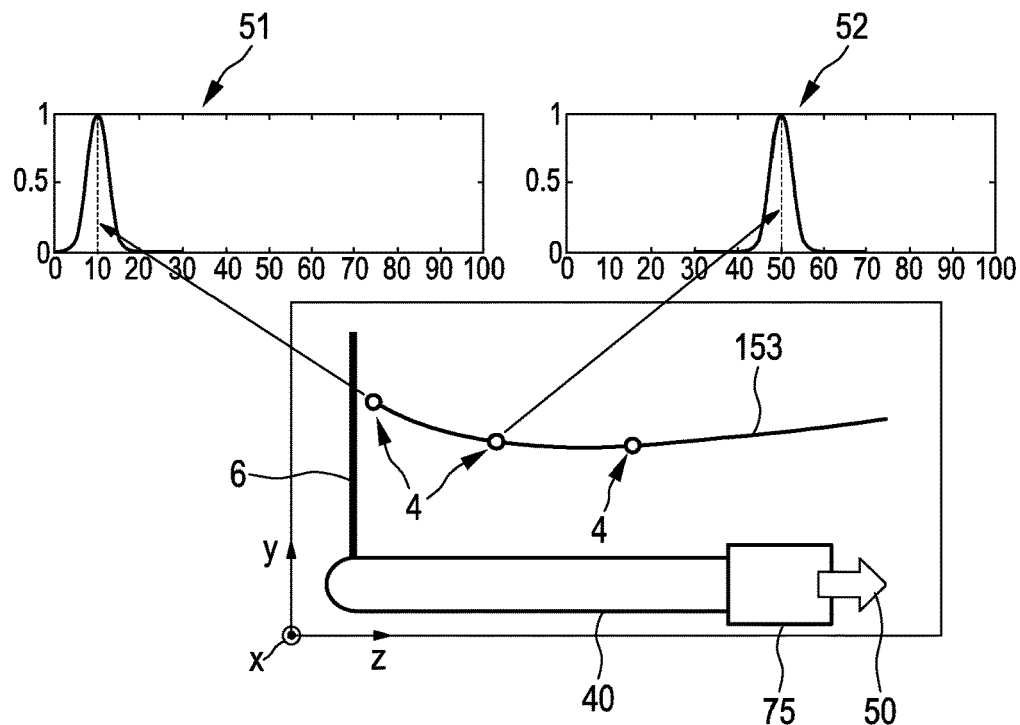
FIG. 8 illustrates exemplarily an embodiment of determining positions of ultrasound sensors of a guidewire by using a TRUS probe being capable of two-dimensional imaging.

Thus, as exemplarily illustrated in FIG. 8, which just shows the guidewire 153, i.e. without the respective brachytherapy catheter in which the guidewire 153 has been inserted, for clarity reasons, the TRUS probe 40 being, in this embodiment, capable of two-dimensional imaging only, can be moved in the direction indicated by reference number 50 parallel to the z direction, in order to move the imaging plane 6, which is parallel to the x-y-plane, in the z direction. If the imaging plane 6 passes the ultrasound sensor 4, which is arranged at the left side in FIG. 8, the ultrasound signal 51 may be generated, and, if the imaging plane 6 passes the ultrasound sensor 4, which is subsequent to the left sensor 4 in FIG. 8, the ultrasound signal 52 may be generated. Since the position of the imaging plane 6 at the point in time, at which the respective ultrasound signal 51, 52 is generated, is determined and since also the position of the respective ultrasound sensor 4 within the imaging plane 6 at this point in time is determined, information is provided, which allows the position determining unit 44 to determine the position of the respective ultrasound sensor 4 in three-dimensional space, wherein the resulting three-dimensional positions of the ultrasound sensors 4 can be used to determine the three-dimensional pose and shape of the respective brachytherapy catheter.

This procedure is suited for pre-procedural brachytherapy catheter mapping, wherein preferentially the guidewire 153 is fully inserted into the respective brachytherapy catheter and fixed and wherein the guidewire 153 comprises one ultrasound sensor 4 at its tip and the other ultrasound sensors distributed along the length of the guidewire 153. The TRUS probe 40 may be mounted on an encoder to access the third dimension, i.e. the imaging plane position providing unit 75 may be an encoder providing in this embodiment the z position of the imaging plane 6 being arranged in a plane that is parallel to the x-y-plane. The TRUS probe 40 is retracted and the ultrasound signal generated by the respective ultrasound sensor 4 is used to detect whether the respective ultrasound sensor 4 is in the two-dimensional imaging plane 6 or not. In other embodiments the position of the imaging plane 6 may also be modified in another way, for instance, the imaging plane may be rotated, wherein also in this case the imaging plane position providing unit is adapted to determine the respective actual position of the imaging plane.

Figure 9:
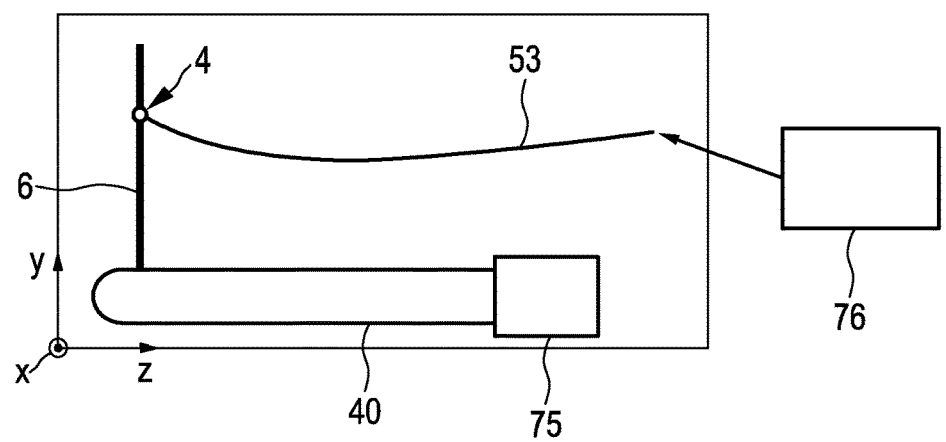
FIG. 9 illustrates exemplarily an embodiment of determining positions of an ultrasound sensor of a guidewire by using a TRUS probe being capable of two-dimensional imaging.

In a further embodiment the guidewire 53 equipped with a single ultrasound sensor 4 at its tip as schematically and exemplarily illustrated in FIG. 5 is used together with the two-dimensional TRUS probe 40 for determining the three-dimensional pose and shape of the respective brachytherapy catheter. Also in this embodiment the two-dimensional TRUS probe 40 is adapted to modify the position of its imaging plane 6, in order to send ultrasound radiation into different regions within the person 2 for allowing the ultrasound sensor 4 at the tip of the guidewire 53 to generate the ultrasound signals, while the ultrasound sensor 4 is at the different positions within the respective brachytherapy catheter during the insertion and/or refraction of the guidewire 53. As schematically and exemplarily illustrated in FIG. 9, a guidewire control unit 76 may control the insertion and/or retraction of the guidewire 53 based on the respective position of the imaging plane 6 provided by the imaging plane position providing unit 75 and/or based on the ultrasound signal generated by the ultrasound sensor 4, which the guidewire control unit 76 may receive via the position determining unit 44, such that the ultrasound sensor 4 remains within the imaging plane 6, when the position of the imaging plane 6 is modified. Also in this example the position determining unit 44 is adapted to determine the positions of the ultrasound sensor 4 based on the generated ultrasound signals and the provided respective positions of the imaging plane 6, wherein the three-dimensional pose and shape of the respective brachytherapy catheter is determined based on the determined different positions of the ultrasound sensor 4.

Thus, the guidewire 53 with the single ultrasound sensor 4 may be used in a closed loop control, in order to map the three-dimensional pose and shape of the brachytherapy catheter using the two-dimensional TRUS probe 40. The guidewire control unit 76 preferentially comprises a motor for inserting and/or retracting, respectively, the guidewire 53 and a controller for controlling the motor in a way that the ultrasound sensor 4 is always in the imaging plane 6, i.e. in the two-dimensional ultrasound image generated by using the ultrasound data from the moving TRUS probe 40. The TRUS probe 40 is preferentially translated along the z-axis, i.e. perpendicular to the imaging plane 6, manually or automatically. However, the TRUS probe 40 can also be moved in another way for modifying the position of the imaging plane 6, for instance, it can be rotated. The two-dimensional positions of the ultrasound sensor 4 detected in the TRUS image are combined with the positions of the tracked TRUS probe 40 to reveal the three-dimensional positions of the ultrasound sensor 4 during the insertion and/or retraction of the guidewire 53. This technique is suited for pre-procedural brachytherapy catheter mapping.

Also the positions of the ultrasound sensors 4 of the brachytherapy catheter 112 schematically and exemplarily illustrated in FIG. 7 can be determined by using a TRUS probe 40 being capable of two-dimensional imaging only, wherein a technique can be used, which is similar to the technique described above with reference to FIG. 8, i.e. similar to the detection of the positions of the ultrasound sensors 4 of the guidewire 153. In particular, all brachytherapy catheters 112 used for the HDR brachytherapy procedure in this example are equipped with multiple ultrasound sensors 4, wherein the position of the imaging plane of the TRUS probe 40 is modifiable, in order to send ultrasound radiation into different regions within the person 2 for allowing the several ultrasound sensors 4 to generate ultrasound signals based on the ultrasound radiation sent by the TRUS probe 40 and received by the respective ultrasound sensor 4. An imaging plane position providing unit, which is preferentially a position encoder, on which the TRUS probe 40 may be mounted, provides the respective position of the imaging plane, wherein the position determining unit 44 can be adapted to determine the positions of the ultrasound sensors 4 of the respective brachytherapy catheter 112 based on the respective ultrasound signals generated by the ultrasound sensors 4 and the respective position of the imaging plane and to determine the three-dimensional pose and shape of the respective brachytherapy catheter 112 based on the determined positions of the ultrasound sensors 4 of the respective brachytherapy catheter 112.

Thus, an encoded TRUS probe 40 may be used to access the third dimension, in order to detect the three-dimensional positions of the ultrasound sensors 4, wherein the TRUS probe 40 may be moved, in particular, retracted, and the ultrasound signal received by each ultrasound sensor 4 may be used to detect whether the respective ultrasound sensor 4 is in the imaging plane, i.e. in the two-dimensional TRUS image. When the respective ultrasound sensor 4 is within the two-dimensional TRUS image, its location within the two-dimensional TRUS image is combined with the position of the imaging plane, in order to reveal the respective three-dimensional position of the respective ultrasound sensor 4. A constrained optimization algorithm, i.e. a constrained fitting algorithm for fitting a curve to the determined positions to the ultrasound sensors 4 of the respective brachytherapy catheter 112, can be used to determine the three-dimensional pose and shape of the respective brachytherapy catheter 112 from the individual determined ultrasound sensor positions. This technique allows for a realtime determination of the three-dimensional poses and shapes of the brachytherapy catheters 112, without needing to insert and/or retract, for instance, a tracked guidewire. Moreover, the three-dimensional poses and shapes of the brachytherapy catheters 112 can be monitored during treatment delivery, particularly for checking for deviations from a pre-delivery configuration.

In addition to determining the pose and shape of the respective brachytherapy catheter within the person 2 based on the determined positions of the respective ultrasound sensor 4, or as an alternative to this determination of the pose and shape of the respective brachytherapy catheter, the position determining unit 44 can be adapted to determine the position of the radiation source 10, when the introduction element has been introduced into the respective brachytherapy catheter, based on the determined positions of the respective ultrasound sensor. In particular, the respective introduction element with the respective radiation source may be equipped with one or several ultrasound sensors such that the one or several ultrasound sensors are arranged at the location of the respective brachytherapy catheter, when the respective introduction element has been introduced into the respective brachytherapy catheter, wherein the positions of the one or more ultrasound sensors can be determined, when the respective introduction element has been introduced into the respective brachytherapy catheter, and wherein the position of the radiation source 10 can be determined based on the determined positions of the one or several ultrasound sensors. An introduction element, which may also be regarded as being a source cable, equipped with an ultrasound sensor and a radiation source is schematically and exemplarily illustrated in FIG. 10.

Figure 10:
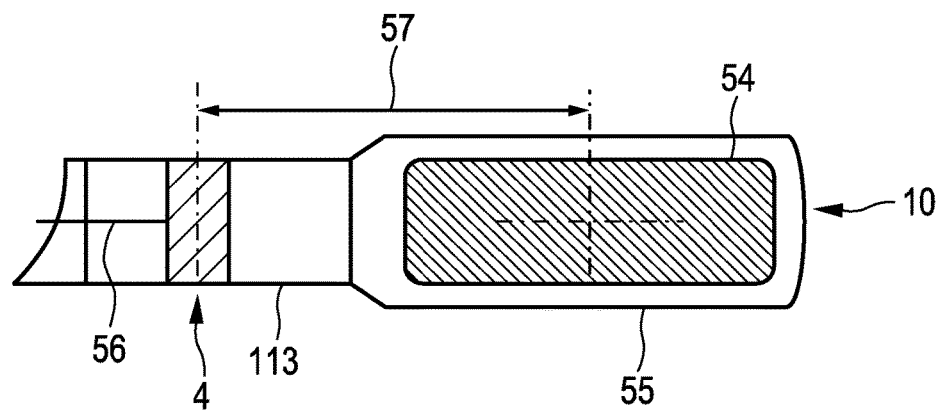
FIG. 10 shows schematically and exemplarily an embodiment of an introduction element with an ultrasound sensor and a radiation source.

The introduction element 113 comprises an ultrasound sensor 4 for generating an ultrasound signal based on ultrasound radiation sent by the TRUS probe 40 and received by the ultrasound sensor 4. The ultrasound signal is transmitted to the position determining unit 44 via an electrical connection 56. At the tip of the introduction element 113 the radiation source 10 is arranged, which comprises a capsule 55, which is preferentially a stainless steel capsule, with radioactive material 54. The position determining unit 44 can be adapted to determine the position of the radiation source 10, when the respective introduction element 113 has been introduced into the respective brachytherapy catheter 12, based on the ultrasound signal generated by the ultrasound sensor 4 and based on a spatial relation between the ultrasound sensor 4 and the radiation source 10 provided by a spatial relation providing unit 74. In this example the provided spatial relation is the spatial offset 57 between the longitudinal center of the ultrasound sensor 4 and the longitudinal center of the radioactive material 54 as illustrated in FIG. 10. In particular, the position determining unit 44 is adapted to determine the position of the ultrasound sensor 4, when the respective introduction element 113 has been introduced into the respective brachytherapy catheter 12, based on the generated ultrasound signal and to determine the position of the radiation source 10 depending on the determined position of the ultrasound sensor 4 of the respective introduction element 113 and on the spatial offset 57 between the ultrasound sensor 4 and the radiation source 10 of the respective introduction element 113. The spatial offset 57, which can also be regarded as being a linear offset, between the ultrasound sensor 4 and the radiation source 10 can be measured in advance and stored in the spatial relation providing unit 74, in order to allow the spatial relation providing unit 74 to provide the linear offset 57. The position of the ultrasound sensor 4 within the respective brachytherapy catheter 12 may be determined in realtime such that also the position of the radiation source 10 within the respective brachytherapy catheter 12 can be determined in realtime by adding the linear offset 57 to the determined position of the ultrasound sensor 4.

Figure 11:
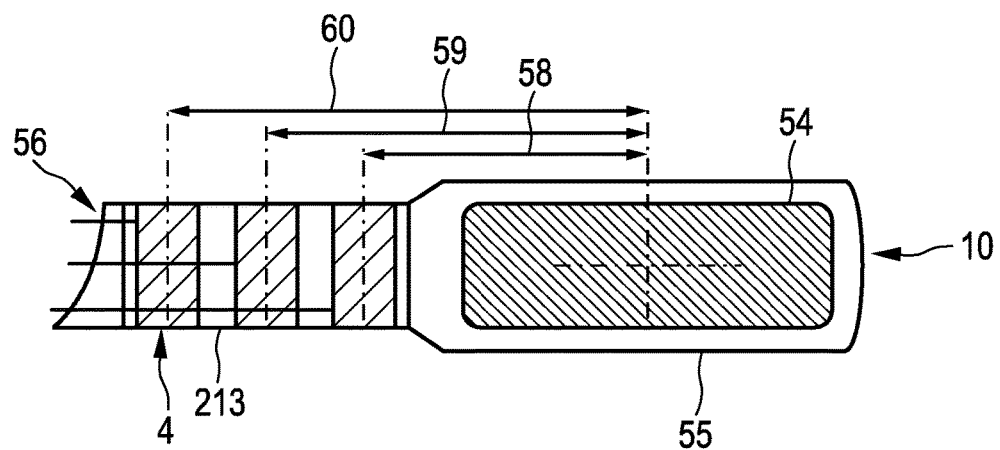
FIG. 11 shows schematically and exemplarily a further embodiment of an introduction element with several ultrasound sensors and a radiation source.

In a further embodiment the introduction element can comprise several ultrasound sensors as schematically and exemplarily illustrated in FIG. 11. The introduction element 213 comprises several ultrasound sensors 4 having different offsets 58, 59, 60 to the radiation source 10 which includes a capsule 55, which is rigidly attached to the introduction element 213, and radioactive material 54 within the capsule 55. Also in this embodiment the ultrasound sensors 4 are electrically connected with the position determining unit 44 by electrical connections 56 for transmitting ultrasound signals generated by the ultrasound sensors 4 to the position determining unit 44. The linear offsets 58, 59, 60 of the ultrasound sensors 4 to the radiation source 10 are known from pre-interventional measurements and stored in the spatial relation providing unit 74, in order to allow the spatial relation providing unit 74 to provide the linear offsets 58, 59, 60 as spatial relations to the position determining unit 44. Using several ultrasound sensors 4 attached to the respective introduction elements 113 with known linear offsets 58, 59, 60 to the radiation source 10 and thus with known linear offsets between the several ultrasound sensors 4 can make the determination of the position of the radiation source 10 more robust. In particular, the position determining unit 44 can be adapted to determine the positions of the several ultrasound sensors 4 based on the ultrasound signals generated by the ultrasound sensors 4 and to linearly extrapolate the determined positions of the ultrasound sensors 4, in order to determine the position of the radiation source 10. An advantage of having multiple sensors is that there is no ambiguity in determining the direction of the radiation source position during the extrapolation process. The HDR brachytherapy system 1 further comprises a display 30 for displaying the determined positions on the ultrasound image generated from the ultrasound data of the TRUS probe 40. The display 30 can show the determined three-dimensional poses and shapes of the brachytherapy catheters and/or the determined three-dimensional position of the radiation source.

The HDR brachytherapy system 1 further comprises a treatment plan providing unit 39 for determining a treatment plan defining dwell positions and dwell times of the radiation sources 10 within the prostate 11, wherein the treatment plan providing unit 39 is adapted to segment the prostate 11 in the ultrasound image and to determine the treatment plan based on the segmented image and the poses and shapes of the brachytherapy catheters. In particular, the treatment plan providing unit 39 is adapted to determine the pose and shape of the prostate 11 from the segmented image and to determine the treatment plan based on the pose and shape of the prostate 11 and the poses and shapes of the brachytherapy catheters. The dwell positions define where the radiation sources 10 are to be placed and the dwell times define when and how long the respective radiation source 10 is to be placed at the respective dwell position.

The brachytherapy system 1 further comprises a placing control unit 15 for controlling the placing unit 5 depending on the determined treatment plan. Alternatively, the placing unit 5 may be used manually in accordance with the determined treatment plan, wherein a user may move the radiation sources 10 via the wires, i.e. via the introduction elements, within the brachytherapy catheters in accordance with the treatment plan. The placing unit 5 and the placing control unit 15 can be regarded as forming a brachytherapy application unit for applying the brachytherapy in accordance with the treatment plan.

Also the planned dwell positions as defined by the treatment plan may be shown on the generated ultrasound image. In particular, the respective realtime position of the respective radiation source may be superimposed on a live two-dimensional or three-dimensional TRUS image together with planned source trajectories as defined by the planned dwell positions, in order to allow a user to visually compare planned and actual radiation source positions. This can give the user confidence that the radiation dose is being delivered as intended during treatment delivery. If deviations are noted in the actual radiation source positions compared to the planned dwell positions, the HDR brachytherapy treatment may be stopped automatically or manually by the user and the respective radiation source may be temporarily retracted.

Moreover, the treatment plan providing unit 39 can be adapted to modify the treatment plan based on the determined real dwell positions, i.e. based on the determined real positions of the respective radiation source during the HDR brachytherapy procedure, if deviations between the planned dwell positions and the real dwell positions are larger than a predetermined threshold value, or if the user indicates to the treatment plan providing unit 39 that the treatment plan should be modified based on the determined real dwell positions. The HDR brachytherapy system can comprise an input unit like a keyboard, a computer mouse, a touch screen, et cetera, in order to allow the user to, for instance, indicate that the treatment plan providing unit 39 should modify the treatment plan based on the determined real dwell positions.

The treatment plan providing unit 39 may be adapted to modify the treatment plan by, if required, modifying the future planned dwell positions defined by the original treatment plan. In particular, the treatment plan may be adapted in realtime during treatment delivery, wherein the determined actual radiation source positions can be fed back in realtime to the treatment planning system, i.e. to the treatment plan providing unit 39. For instance, the treatment plan providing unit 39 can be adapted to recompute the three-dimensional radiation dose distribution within the person 2 in realtime using a) the already achieved dwell positions and dwell times, which have been detected so far, b) the current radiation source position, and c) future expected dwell positions and dwell times defined by the current treatment plan. Based on this realtime recomputed radiation dose distribution, i.e. based on the realtime recomputed dose map, the treatment plan providing unit 39 can adapt the treatment plan by modifying the future dwell positions and dwell times to ensure that the target, which has been segmented in the ultrasound image, receives a desired radiation dose and surrounding elements, which may also be segmented in the ultrasound image, like organs at risk receive a minimal radiation dose only. Thus, the future dwell positions and dwell times of the radiation source can be modified accordingly, in order to achieve this goal based on the realtime recomputed radiation dose distribution, i.e. the treatment plan providing unit 39 can be adapted to determine whether the realtime recomputed radiation dose distribution fulfills predefined dose requirements and, if this is not the case, modify the future dwell positions and dwell times and correspondingly recompute the radiation dose distribution such that it fulfills the predefined dose requirements.

In addition to or as an alternative to using the real radiation source positions for updating the treatment plan, the real radiation source positions determined by the position determining unit 44 can also be provided to the placing control unit 15, which can also be regarded as being an introduction element controller, in order to allow the placing control unit 15 to move the respective radiation source 10 within the respective brachytherapy catheter based on the respective actual real position of the respective radiation source such that it corresponds to the desired planned dwell position. Thus, the realtime position information from the position determining unit 44, which has been determined based on the ultrasound signal generated by the respective ultrasound sensor, can be fed back to the placing control unit 15, in order to allow the placing control unit 15 to move the respective radiation source to the respective next planned dwell position as defined by the treatment plan, wherein this treatment plan can be the original treatment plan or an amended treatment plan, which has been determined based on the updated three-dimensional radiation dose distribution.

In a further embodiment one or several ultrasound sensors attached to a brachytherapy catheter may be used for determining the position of the radiation source within the respective brachytherapy catheter, after the introduction element with the radiation source has been introduced into the respective brachytherapy catheter. For instance, a single ultrasound sensor 4 may be arranged at the tip of the respective brachytherapy catheter, wherein the spatial relation providing unit 74 may be adapted to provide a spatial relation between the ultrasound sensor 4 and the radiation source 10, when the introduction element has been introduced into the respective brachytherapy catheter completely, i.e. as far as possible, wherein the position determining unit 44 can be adapted to determine the position of the radiation source 10, when the introduction element has been introduced into the respective brachytherapy catheter completely, based on the generated ultrasound signal and the provided spatial relation. In particular, the position determining unit 44 can be adapted to determine the position of the ultrasound sensor of the brachytherapy catheter, when the introduction element has been introduced into the brachytherapy catheter completely, and to determine the position of the radiation source based on the determined position of the ultrasound sensor and a spatial relation between the position of the ultrasound sensor and the position of the radiation source, which may be a predetermined linear offset between the ultrasound sensor and the radiation source. Also radiation source position information from the placing unit 5, which may be regarded as being an afterloader, can be used for determining the position of the radiation source. In particular, the spatial relation providing unit 74 can be adapted to determine the spatial relation between the ultrasound sensor 4 and the radiation source 10 depending on the actual position of the introduction element relative to the brachytherapy catheter provided by the placing unit 5 and a known spatial relation between the ultrasound sensor 4 and the brachytherapy catheter, wherein this spatial relation between the ultrasound sensor 4 and the radiation source 10 can be used to determine the position of the radiation source 10 based on the determined position of the ultrasound sensor 4. Also an already determined pose and shape of a brachytherapy catheter, which has been determined based on one or several positions of one or several ultrasound sensors, can be used together with the actual spatial relation between the introduction element comprising the radiation source and the brachytherapy catheter, which may be provided by the placing unit 5, for determining the actual position of the radiation source.

In a further embodiment the brachytherapy catheter may be equipped with an ultrasound sensor at a longitudinal position of the brachytherapy catheter such that at least a part of the radiation source is arrangeable at this longitudinal position, at which the ultrasound sensor is located, when the introduction element comprising the radiation source is introduced into the brachytherapy catheter. The position determining unit 44 can then be adapted to detect a change of the generated ultrasound signal, when the radiation source is arranged at the longitudinal position, at which the ultrasound sensor is located, and to determine the position of the radiation source based on the determined position of the ultrasound sensor and the detected change of the ultrasound signal. In particular, as schematically and exemplarily illustrated in FIG. 12, an ultrasound sensor 4 can be incorporated on the outside of a brachytherapy catheter 212 with an offset 82 from the conical brachytherapy catheter tip. This offset 82 is preferentially chosen such that, when the radiation source 10 with the radioactive material 54 and the capsule 55 is at its first dwell position, the tip of the source train, i.e. the tip of the capsule 55, is alongside the ultrasound sensor 4. For instance, if the offset 61 between the center of the radioactive material 54 at the first dwell position and the tip of the brachytherapy catheter is 6 mm and if the distance 81 between the center of the radioactive material 54 and the edge of the source train, i.e. of the tip of the capsule 55, is 4 mm, the ultrasound sensor 4 may be arranged such that the distance 82 between the center of the ultrasound sensor 4 and the brachytherapy catheter tip is 2 mm.

Figure 12:
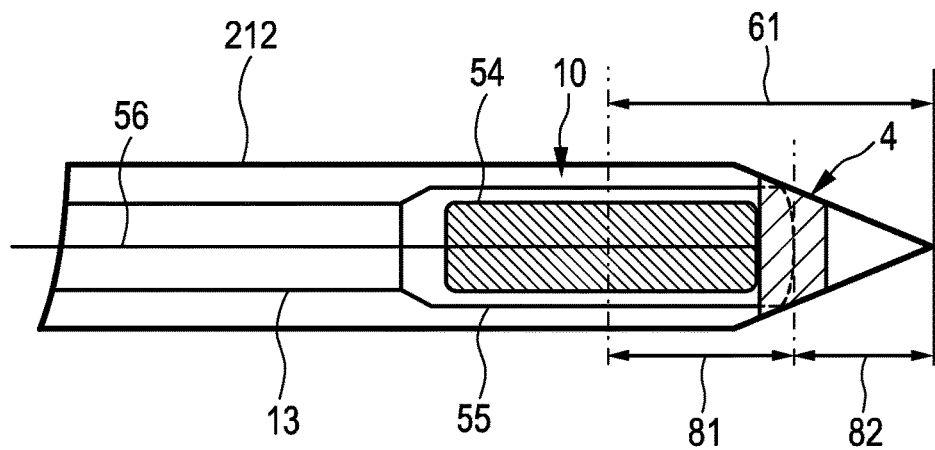
FIG. 12 shows schematically and exemplarily an embodiment of a brachytherapy catheter with an ultrasound sensor, wherein an introduction element with a radiation source has been introduced into the brachytherapy catheter.

During treatment delivery, when the radiation source 10 is at its first dwell position schematically and exemplarily illustrated in FIG. 12, the tip of the source train, i.e. the tip of the capsule 55, is under the ultrasound sensor 4. This leads to a change in the ultrasound signal generated by the ultrasound sensor 4 such that this signal change can be used to detect that the radiation source 10 is at its first dwell position. The signal change is illustrated in FIGS. 13 and 14.

Figures 13, 14:
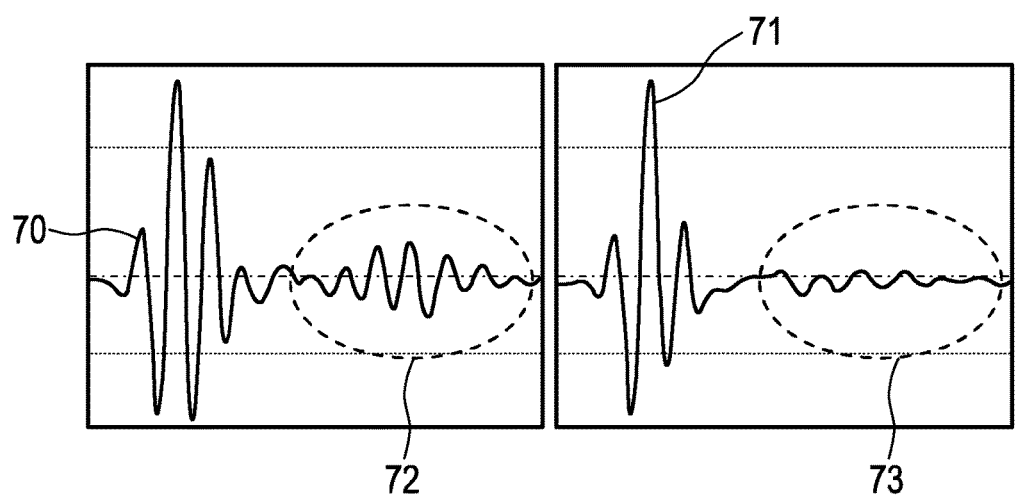
FIGS. 13 and 14 illustrate exemplarily ultrasound signals generated by an ultrasound sensor attached to a brachytherapy catheter.

FIGS. 13 and 14 show exemplarily ultrasound signals 70, 71, which may be generated by the ultrasound sensor 4. The ultrasound signal 70 shown in FIG. 13 has been generated, while the radiation source 10 was not arranged at the linear position of the ultrasound sensor 4, i.e. while the tip of the source train was not under the ultrasound sensor 4, and the ultrasound signal 71 shown in FIG. 14 has been generated, while the radiation source 10 was arranged at the linear position of the ultrasound sensor 4, i.e. while the tip of the source train was under the ultrasound sensor 4. The ellipses 72, 73 illustrate the signal change.

Thus, during treatment delivery the response from the ultrasound sensor 4 can be monitored in realtime, wherein, when the radiation source 10 has been positioned at its first dwell position, the ultrasound sensor 4 should indicate this via the change in the signal pattern as illustrated in FIGS. 13 and 14. If this is not the case, i.e. if such a signal change is not detected, although the radiation source 10 is supposed to be arranged at its first dwell position, the ultrasound imaging and the placing of the radiation source are not accurately registered or other inaccuracies may be present. The treatment may then be stopped and corrective measures may be taken like checking connections between the placing unit and the brachytherapy catheters, verifying the treatment plan used by the placing unit, et cetera.

Since the observation of the signal change, when the radiation source is supposed to be arranged at its first dwell position, allows for an intra-procedural determination of inaccuracies, this monitoring of the signal change may be regarded as being an intra-procedural quality assurance technique, which can allow for a further improved accuracy of the HDR brachytherapy.

Since the prostate has been segmented in the ultrasound image, which has been generated by using the TRUS probe, and since the poses and shapes of the brachytherapy catheters have been determined based on positions of ultrasound sensors, which have also been determined with respect to the ultrasound image, the pose and shape of the segmented prostate and the poses and shapes of the brachytherapy catheters are both known relative to the ultrasound image. The treatment plan providing unit 39 can therefore determine the treatment plan defining the dwell positions and the dwell times of the radiation sources 10 depending on the spatial relationship between the pose and shape of the prostate 11 and the poses and shapes of the brachytherapy catheters. A registration of theses poses and shapes is not required. For planning the different dwell positions and dwell times known planning techniques can be used like the planning technique disclosed in the article "Optimization of HDR brachytherapy dose distributions using linear programming with penalty costs" by Ron Alterovitz et al., Medical Physics, volume 33, number 11, pages 4012 to 4019, November 2006, which is herewith incorporated by reference.

Figure 15:
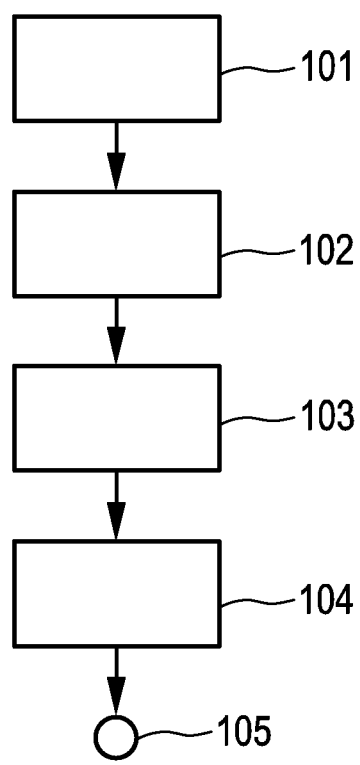
FIG. 15 shows a flowchart exemplarily illustrating an embodiment of a HDR brachytherapy method for performing a HDR brachytherapy.

In the following an embodiment of a HDR brachytherapy method for performing a HDR brachytherapy will exemplarily be described with reference to a flowchart shown in FIG. 15.

After the brachytherapy catheters have been inserted into the prostate 11 of the person 2, for instance, under guidance of an ultrasound image generated by the ultrasound image generating unit 42 based on ultrasound data received from the TRUS probe 40, in step 101 the TRUS probe 40 sends ultrasound radiation to the inside of the person 2 and measures ultrasound radiation reflected by the inside of the person 2 and the ultrasound image generating unit 42 generates an ultrasound image based on the reflected ultrasound radiation. Moreover, ultrasound signals are generated by one or several ultrasound sensors 4, which are arranged at the locations of the brachytherapy catheters within the person 2, wherein the one or several ultrasound sensors 4 generate the ultrasound signals based on the ultrasound radiation sent by the TRUS probe 40 and received by the one or several ultrasound sensors 4. The ultrasound sensors may be arranged at the locations of the brachytherapy catheters, because the brachytherapy catheters may be equipped with the one or several ultrasound sensors 4 and/or because a guidewire equipped with the one or several ultrasound sensors may have been inserted into the brachytherapy catheters. If the one or several ultrasound sensors 4 are arranged at the locations of the brachytherapy catheters by using the guidewire equipped with the one or several ultrasound sensors, the guidewire is preferentially sequentially inserted into the different brachytherapy catheters, wherein the ultrasound signals are generated, when the guidewire is within the different brachytherapy catheters.

In step 102 the position determining unit 44 determines the positions of the one or several ultrasound sensors 4 based on the generated ultrasound signals and determines the three-dimensional poses and shapes of the brachytherapy catheters within the person 2 based on the determined positions of the one or several ultrasound sensors 4 arranged at the locations of the brachytherapy catheters within the person 2.

In step 103 the treatment plan providing unit 39 segments the prostate 11 within the generated ultrasound image, in order to determine the three-dimensional pose and shape of the prostate 11, and determines an initial treatment plan defining dwell positions and dwell times of the radiation sources 10 within the brachytherapy catheters based on the three-dimensional poses and shapes determined in step 102 and based on the determined three-dimensional pose and shape of the segmented prostate 11.

In step 104 the brachytherapy application unit applies a brachytherapy in accordance with the treatment plan, i.e. it places the radiation sources within the brachytherapy catheters in accordance with the dwell positions and dwell times defined by the treatment plan, wherein, after the HDR brachytherapy has been performed in accordance with the treatment plan, the HDR brachytherapy method ends in step 105.

During the placing of the radiation sources at the dwell positions and dwell times defined by the treatment plan in step 104, the three-dimensional poses and shapes of the brachytherapy catheters may be continuously monitored, wherein in this case the brachytherapy catheters and/or the introduction elements with the radiation sources are equipped with one or several ultrasound sensors. Moreover, in step 104 also the positions of the radiation sources may be monitored based on one or several ultrasound sensors attached to the brachytherapy catheters and/or to the introduction elements. The monitored three-dimensional poses and shapes of the brachytherapy catheters and/or the monitored three-dimensional positions of the radiation sources can be used for updating the treatment plan in step 104 in a closed loop such that the HDR brachytherapy can account for, for instance, edema or other causes of pose and shape changes.

The position determining unit 44 is adapted to determine the position of the respective ultrasound sensor in the field of view of the TRUS probe 40 by analyzing the ultrasound signal generated by the respective ultrasound sensor as ultrasound beams of the TRUS probe sweep the field of view. The time-of-flight can be determined for providing the axial and radial distance of the respective ultrasound sensor from the imaging array of the TRUS probe, while the amplitude of the generated ultrasound signal and the knowledge of the beam firing sequence can provide the lateral and angular position of the respective ultrasound sensor. If the TRUS probe is a three-dimensional TRUS probe, the elevational position of the respective ultrasound sensor can also be obtained in a similar manner. Thus, the position determining unit 44 can determine the two-dimensional position of the respective ultrasound sensor in the imaging plane, if the TRUS probe is a two-dimensional TRUS probe, and the three-dimensional position of the respective ultrasound sensor within the field of view of the TRUS probe, if the TRUS probe is a three-dimensional TRUS probe, based on the ultrasound signal generated by the respective ultrasound sensor. For more details regarding the determination of the position of the respective ultrasound sensor based on the generated ultrasound signals, which are generated, when the respective ultrasound sensor receives ultrasound radiation from the TRUS probe, reference is made to, for instance, the article "A Non-disruptive Technology for Robust 3D Tool Tracking for Ultrasound-Guided Interventions" by Jay Mung et al., *Medical Image Computing and Computer-Assisted Intervention MICCAI* 2011, *Lecture Notes in Computer Science*, volume 6891, pages 153 to 160 (2011), which is herewith incorporated by reference.

The TRUS probe can be adapted to generate B-mode ultrasound images. The ultrasound sensors may comprise piezoelectric materials like PZT, polyvinylidene fluoride (PVDF), piezoelectric copolymers, et cetera.

Manual ultrasound-based brachytherapy catheter segmentation and tracking is an error-prone and time-consuming process, due to inferior ultrasound image quality and also because the brachytherapy catheters closer to the TRUS probe cause shadowing artifacts that hamper the detection of brachytherapy catheters further away from the TRUS probe. Electromagnetically determining the poses and shapes of the brachytherapy catheters by using electromagnetically tracked guidewires can improve the brachytherapy segmentation and tracking, but the electromagnetic solution requires the placement of an electromagnetic field generator close to the anatomy, which should be treated. This can be cumbersome in a clinical HDR brachytherapy setup and the electromagnetic technology is also susceptible to distortions caused by a possible presence of metallic elements. In contrast, the ultrasound tracking technology described above with reference to FIGS. 1 to 15 is more accurate and cheaper than the electromagnetic based solution and is free of cumbersome hardware, i.e. is clinically easier to use. For instance, for the determination of the three-dimensional poses and shapes of the brachytherapy catheters just a guidewire equipped with one or more ultrasound sensors may be used, wherein the guidewire may be sequentially inserted into and retracted from the different brachytherapy catheters and simultaneously the positions of the one or several ultrasound sensors can be determined during the insertion and/or retraction. Based on these positions of the ultrasound sensors the three-dimensional pose and shape of the respective brachytherapy catheter can be determined. If the guidewire comprises several ultrasound sensors, the three-dimensional pose and shape of the respective brachytherapy catheter may also be determined during a one-time pre-procedural step, in which the guidewire has been introduced into the respective brachytherapy catheter and remains static within the respective brachytherapy catheter during the determination of the positions of the ultrasound sensors. If the brachytherapy catheters are equipped with multiple ultrasound sensors, the three-dimensional poses and shapes of the brachytherapy catheters can be tracked in realtime at all times, thereby obviating the need for having a tracked guidewire.

The automated ultrasound-based three-dimensional mapping of the brachytherapy catheters can be useful in simplifying existing clinical HDR brachytherapy workflows, can make the process of brachytherapy catheter mapping more accurate, user-independent and easy to implement. The tracked positions are inherently registered to the TRUS images. Therefore, the user, which may be a clinician or a physicist, does not need to explicitly calibrate the HDR brachytherapy system before each use, thereby increasing its acceptability in the clinic.

Known brachytherapy treatments often proceed on the basis of the assumption that there is no relative motion between the brachytherapy catheters and the anatomy between the time of the brachytherapy catheter and target segmentation and treatment delivery. Tissue edema, however, may result in unexpected changes in relative brachytherapy catheter positions and correspondingly in unexpected changes in radiation source positions. Above described embodiments provide therefore a direct, reliable and realtime tracking of the position of the radioactive source relative to the anatomy during the treatment delivery. Since ultrasound tracking technology is used for determining the position of the radiation source, no additional registration is needed between the tracked radiation source positions and the surrounding anatomy as seen on the ultrasound images.

Although in above described embodiments the HDR brachytherapy is used for applying radiation to the prostate, in other embodiments the HDR brachytherapy can also be used to apply radiation to another part of a person or an animal. Moreover, although in above described embodiments the ultrasound imaging device uses a TRUS probe for generating the ultrasound image, in other embodiments another kind of an ultrasound imaging device can be used for generating an ultrasound image by sending ultrasound radiation into the inside of a living being and by measuring ultrasound radiation reflected by the inside of the living being, wherein an ultrasound sensor arranged at the location of the respective brachytherapy catheter generates an ultrasound signal based on ultrasound radiation sent by the ultrasound imaging device and received by the ultrasound sensor.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the positions of the one or several ultrasound sensors, the determination of the pose and shape of the brachytherapy catheter, the determination of the position of the radiation source, the determination of the treatment plan, the adaptation of the treatment plan, et cetera performed by one or several units or devices can also be performed by any other number of units or devices. These procedures and/or the control of the HDR brachytherapy system in accordance with the HDR brachytherapy method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a HDR brachytherapy system comprising an ultrasound sensor for being arranged at the location of a brachytherapy catheter, wherein the ultrasound sensor is adapted to generate an ultrasound signal based on ultrasound radiation, which has been sent by an ultrasound imaging device preferentially comprising a TRUS probe and which has been received by the ultrasound sensor. The position of the ultrasound sensor is determined based on the generated ultrasound signal, and based on this position of the ultrasound sensor the pose and shape of the brachytherapy catheter and/or the position of a HDR radiation source are determined. This allows for a very accurate determination of the pose and shape of the brachytherapy catheter and/or of the position of the HDR radiation source, which in turn can lead to an improved HDR brachytherapy.

The invention claimed is:

1. A high-dose rate brachytherapy system for performing high-dose rate brachytherapy, the high-dose rate brachytherapy system comprising:
    a brachytherapy catheter to be inserted into or adjacent a target region inside a living being,
    an elongated introduction element with a radiation source for applying radiation emitted by the radiation source to the target region, wherein the brachytherapy catheter and the introduction element are adapted to allow the introduction element to be introduced into the brachytherapy catheter,
    an ultrasound imaging device for generating an ultrasound image of the inside of the living being by sending ultrasound radiation into the inside of the living being and by measuring ultrasound radiation reflected by the inside of the living being,
    an ultrasound sensor for being arranged at a location of the brachytherapy catheter within the living being, wherein the ultrasound sensor is adapted to generate an ultrasound signal based on ultrasound radiation sent by the ultrasound imaging device and received by the ultrasound sensor,
    a position determining unit for determining a position of the ultrasound sensor based on the generated ultrasound signal and for determining pose and shape of the brachytherapy catheter within the living being and/or a position of the radiation source, when the introduction element has been introduced into the brachytherapy catheter, based on the determined position of the ultrasound sensor.

2. The high-dose rate brachytherapy system as defined in claim 1, further comprising:
    a guidewire equipped with the ultrasound sensor, wherein the guidewire is adapted to be inserted into the brachytherapy catheter for arranging the ultrasound sensor at the location of the brachytherapy catheter within the living being, wherein the guidewire is adapted to be inserted into and retracted from the brachytherapy catheter, wherein the ultrasound sensor is adapted to generate ultrasound signals, while the guidewire is inserted into and/or retracted from the brachytherapy catheter, and wherein the position determining unit is adapted to determine different positions of the ultrasound sensor based on the ultrasound signals generated while the guidewire is inserted into and/or retracted from the brachytherapy catheter and to determine the pose and shape of the brachytherapy catheter based on the different positions of the ultrasound sensor.

3. The high-dose rate brachytherapy system as defined in claim 2, wherein the ultrasound imaging device is a two-dimensional ultrasound imaging device for generating a two-dimensional image of an imaging plane within the living being, and wherein a position of the imaging plane is modifiable, in order to send ultrasound radiation into different regions within the living being for allowing the ultrasound sensor to generate the ultrasound signals, while the ultrasound sensor is at the different positions during the insertion and/or retraction of the guidewire.

4. The high-dose rate brachytherapy system as defined in claim 3, further comprising:
an imaging plane position providing unit for determining the position of the imaging plane; and
a guidewire control unit for controlling the insertion and/or retraction of the guidewire based on the determined position of the imaging plane such that the ultrasound sensor is within the imaging plane, when the position of the imaging plane is modified, wherein the position determining unit is adapted to determine the different positions of the ultrasound sensor based on the generated ultrasound signals and the position of the imaging plane.

5. The high-dose rate brachytherapy system as defined in claim 2, wherein the guidewire is equipped with a plurality of ultrasound sensors, wherein each ultrasound sensor is adapted to generate an ultrasound signal based on ultrasound radiation sent by the ultrasound imaging device and received by the ultrasound sensor, wherein the position determining unit is adapted to:
determine for the plurality of ultrasound sensors sets of different positions of the ultrasound sensors, respectively, based on the respective ultrasound signals generated by the ultrasound sensors during the insertion and/or retraction of the guidewire,
determine for each set of different positions of the respective ultrasound sensor a pose and shape of the brachytherapy catheter, thereby determining a set of poses and shapes of the brachytherapy catheter, and
average the poses and shapes of the determined set of poses and shapes of the brachytherapy catheter for determining an average pose and shape of the brachytherapy catheter.

6. The high-dose rate brachytherapy system as defined in claim 1, further comprising a plurality of ultrasound sensors for being arranged along a length of the brachytherapy catheter, wherein each ultrasound sensor is adapted to generate an ultrasound signal based on ultrasound radiation sent by the ultrasound imaging device and received by the respective ultrasound sensor, wherein the position determining unit is adapted to determine positions of the ultrasound sensors based on the ultrasound signals generated by the ultrasound sensors and to determine the pose and shape of the brachytherapy catheter based on the determined positions.

7. The high-dose rate brachytherapy system as defined in claim 6, wherein the ultrasound imaging device is a two-dimensional ultrasound imaging device for generating a two-dimensional image of an imaging plane within the living being, wherein a position of the imaging plane is modifiable, in order to send ultrasound radiation into different regions within the living being for allowing the plurality of ultrasound sensors to generate ultrasound signals based on the ultrasound radiation sent by the ultrasound imaging device and received by the respective ultrasound sensors, wherein the system further comprises an imaging plane position providing unit for determining positions of the imaging plane, wherein the position determining unit is adapted to determine the positions of the ultrasound sensors based on the respective ultrasound signals generated by the ultrasound sensors and the determined positions of the imaging plane.

8. The high-dose rate brachytherapy system as defined in claim 1, wherein the introduction element is equipped with the ultrasound sensor such that the ultrasound sensor is arranged within the brachytherapy catheter, when the introduction element has been introduced into the brachytherapy catheter, wherein the system further comprises a spatial relation providing unit for providing a spatial relation between the ultrasound sensor and the radiation source, wherein the position determining unit is adapted to determine the position of the radiation source, when the introduction element has been introduced into the brachytherapy catheter, based on the generated ultrasound signal and the provided spatial relation.

9. The high-dose rate brachytherapy system as defined in claim 1, further comprising a display for displaying the determined position of the ultrasound sensor on the generated ultrasound image.

10. The high-dose rate brachytherapy system as defined in claim 9, further comprising a treatment plan providing unit for providing a treatment plan defining planned dwell positions within the living being, at which the radiation source should be arranged, wherein the display further displays the planned dwell positions on the generated image.

11. The high-dose rate brachytherapy system as defined in claim 1, further comprising a treatment plan providing unit for providing a treatment plan defining planned dwell positions within the living being, at which the radiation source should be arranged, wherein the position determining unit is adapted to determine positions of the radiation source, when the radiation source is supposed to be placed at the planned dwell positions during the high-dose rate brachytherapy, as real dwell positions, and wherein the treatment plan providing unit is adapted to modify the treatment plan based on the determined real dwell positions.

12. The high-dose rate brachytherapy system as defined in claim 1, further comprising an introduction element controller for controlling the introduction and/or retraction of the introduction element into and/or from, respectively, the brachytherapy catheter based on the determined position of the radiation source.

13. The high-dose rate brachytherapy system as defined in claim 1, wherein the brachytherapy catheter is equipped with the ultrasound sensor, wherein the system further comprises a spatial relation providing unit for providing a spatial relation between the ultrasound sensor and the radiation source, when the introduction element has been introduced into the brachytherapy catheter, wherein the position determining unit is adapted to determine the position of the radiation source, when the introduction element has been introduced into the brachytherapy catheter, based on the generated ultrasound signal and the provided spatial relation.

14. The high-dose rate brachytherapy system as defined in claim 1, wherein the brachytherapy catheter is equipped with the ultrasound sensor at a longitudinal position of the brachytherapy catheter such that the radiation source is arrangeable at the longitudinal position, at which the ultrasound sensor is located, when the introduction element is introduced into the brachytherapy catheter, wherein the position determining unit is adapted to detect a change of the generated ultrasound signal, when the radiation source (10) is arranged at the longitudinal position, at which the ultrasound sensor is located, and to determine the position of the radiation source based on the determined position of the ultrasound sensor and the detected change of the ultrasound signal.

15. A non-transitory computer readable medium comprising instructions for performing high-dose rate brachytherapy which, when executed by a computer, cause the computer to carry out steps comprising:
- generating an ultrasound image of an inside of a living being by sending ultrasound radiation into the inside of the living being and by measuring ultrasound radiation reflected by the inside of the living being by an ultrasound imaging device;
- generating an ultrasound signal by an ultrasound sensor, which is arranged at a location of the brachytherapy catheter within the living being, wherein the ultrasound sensor generates the ultrasound signal based on ultrasound radiation sent by the ultrasound imaging device and received by the ultrasound sensor;
- determining a position of the ultrasound sensor based on the generated ultrasound signal; and
- determining pose and shape of the brachytherapy catheter within the living being and/or a position of a radiation source, when an introduction element has been introduced into the brachytherapy catheter, based on the determined position of the ultrasound sensor by the position determining unit, wherein the introduction element introduces the radiation source for applying radiation to a target region inside of the living being.

* * * * *